US00PP12006P2

(12) United States Plant Patent
VandenBerg

(10) Patent No.: US PP12,006 P2
(45) Date of Patent: Jul. 24, 2001

(54) CHRYSANTHEMUM PLANT NAMED 'YOKEY WEST'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,536

(22) Filed: Aug. 26, 1999

(51) Int. Cl.[7] ..... A01H 5/00
(52) U.S. Cl. ..... Plt./286
(58) Field of Search ..... Plt./286, 295, 296

*Primary Examiner*—Howard J. Locker
(74) *Attorney, Agent, or Firm*—C. A. Whealy

(57) ABSTRACT

A distinct cultivar of Chrysanthemum plant named 'Yokey West', characterized by its upright, outwardly spreading and uniformly mounded plant habit; vigorous and strong growth habit; freely branching habit; strong, dark green foliage; uniform flowering; nine-week response time; numerous large daisy-type inflorescences that are about 7.8 cm in diameter; dark orange to red-colored ray florets with golden yellow longitudinal streaks radiating from the base longitudinally; large disc with green disc florets that are slow to mature to bright yellow; and good postproduction longevity with inflorescences and leaves maintaining good substance and color for about three weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yokey West.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in October, 1994, in Salinas, Calif., of a proprietary *Dendranthema grandiflora* seedling selection identified as YB-5792, as the female, or seed, parent, with a proprietary *Dendranthema grandiflora* seedling selection identified as YB-4369, as the male, or pollen, parent.

The new Chrysanthemum was discovered and selected by the Inventor as a flowering plant within the progeny of the stated cross in a controlled environment in Alva, Fla., in November, 1995. The selection of this plant was based on its desirable inflorescence form and floret colors and good post-production longevity.

Asexual reproduction of the new Chrysanthemum by terminal cuttings harvested in a controlled environment in Alva, Fla., has shown that the unique features of this new Chrysanthemum are stable and reproduced true to type in successive generations.

SUMMARY OF THE INVENTION

The cultivar Yokey West has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yokey West'. These characteristics in combination distinguish 'Yokey West' as a new and distinct Chrysanthemum:

1. Compact; upright, outwardly spreading and uniformly mounded plant habit.

2. Vigorous and strong growth habit.

3. Freely branching habit, full and dense plants.

4. Strong, dark green foliage.

5. Uniform flowering.

6. Nine-week response time.

7. Very freely flowering; numerous large daisy-type inflorescences that are about 7.8 cm in diameter; best produced as a natural spray-type Chrysanthemum.

8. Dark orange to red-colored ray florets with golden yellow longitudinal streaks radiating from the base longitudinally; ray florets held upright.

9. Large disc with green disc florets that are slow to mature to bright yellow.

10. Good postproduction longevity with inflorescences and leaves maintaining good substance and color for about three weeks in an interior environment.

The new Chrysanthemum can be compared to the Chrysanthemum cultivar Tijuana Sunset, disclosed in U.S. Plant Pat. No. 10,462. However in side-by-side comparisons in Salinas, Calif., and Leamington, Ontario, Canada, under commercial practice, plants of the new Chrysanthemum differ from plants of the cultivar Tijuana Sunset in the following characteristics:

1. Plants of the new Chrysanthemum are more vigorous than plants of the cultivar Tijuana Sunset.

2. Plants of the new Chrysanthemum have lighter green and more deeply lobed leaves than plants of the cultivar Tijuana Sunset.

3. Plants of the new Chrysanthemum flower about four or five days later than plants of the cultivar Tijuana Sunset.

4. Ray florets of the new Chrysanthemum are lighter red in color than ray florets of the cultivar Tijuana Sunset.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a side perspective view of a typical flowering plant of 'Yokey West'.

The photograph at the bottom of the first sheet comprises a close-up view of a inflorescence and upper (left) and lower (right) surfaces of typical leaves of the cultivar Yokey West.

The photograph at the top of the second sheet comprises a side perspective view of typical flowering plants of 'Yokey West' (left) and 'Tijuana Sunset' (right).

The photograph at the bottom of the second sheet comprises a close-up view of typical inflorescences of plants of 'Yokey West' (left) and 'Tijuana Sunset' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as natural spray-types. Measurements and numerical values represent averages of typical flowering plants.

Botanical classification: *Dendranthema grandiflora* cultivar Yokey West.

Commercial classification: Daisy spray-type pot Chrysanthemum.

Parentage:

*Female or seed parent.*—Proprietary *Dendranthema grandiflora* seedling selection identified as code number YB-5792.

*Male or pollen parent.*—Proprietary *Dendranthema grandiflora* seedling selection identified as code number YB-4369.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy pot Chrysanthemum typically grown as a spray-type. Inverted triangle; compact growth habit; upright and outwardly spreading giving a uniformly mounded appearance to the plant. Vigorous and strong plants. Freely branching; about four lateral branches develop after removal of terminal apex (pinching); dense and full plants.

*Plant height.*—About 28 cm.

*Plant width.*—About 42 cm.

*Stem color.*—144A.

*Stem texture.*—Pubescent.

*Foliage description.*—Arrangement: Alternate. Length: About 6.75 cm. Width: About 5.6 cm. Apex: Mucronate. Base: Truncate to attenuate. Margin: Palmately lobed, sinuses between lateral lobes parallel to convergent. Texture: Upper and lower surfaces with very fine pubescence; veins prominent on lower surface. Petiole length: About 2.5 cm. Petiole diameter: About 3 mm. Color: Young foliage upper surface: 147A. Young foliage lower surface: 147B. Mature foliage upper surface: 147A. Mature foliage lower surface: 147B. Venation upper surface: 147A. Venation lower surface: 147B.

Inflorescence description:

*Appearance.*—Daisy inflorescence form with elongated-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about nine weeks later.

*Postproduction longevity.*—Inflorescences and leaves will maintain good color and substance for about three weeks in an interior environment.

*Quantity of inflorescences.*—Very freely flowering; about eight inflorescences per lateral branch or about 32 to 35 inflorescences per plant.

*Inflorescence bud.*—Height: About 5 mm. Diameter: About 8 mm. Color: Greener than 143A.

*Inflorescence size.*—Diameter: About 7.8 cm. Depth (height): About 2.2 cm. Diameter of disc: About 1.9 cm.

*Ray florets.*—Shape: Elongated. Orientation: Mostly upright, about 110° to peduncle. Aspect: Straight. Length: About 3.9 cm. Width: About 9 mm. Apex: Pointed or emarginate. Margin: Entire. Texture: Smooth, velvety. Number of ray florets per inflorescence: About 32. Color: When opening: Bright yellow, more intense than 9A; quickly becoming red and yellow. Fully opened, upper surface: Base, yellow, more intense than 9A; mid-section and apex, yellow, more intense than 9A, heavily overlaid with color more orange red than 45A–45B. Iridescent. Fully opened, lower surface: Base, yellow, 9A; mid-section and apex, yellow, 9A, lightly overlaid with red, close to 45A–46A.

*Disc florets.*—Shape: Tubular. Apex: Serrated. Length: About 7.5 mm. Width: Apex, about 1.5 mm; base, about 1 mm. Number of disc florets per inflorescence: Numerous, about 173. Color: Immature: 144A to 154A; slow to mature. Mature: Apex: 7A to 9A. Mid-section: Light green. Base: White, 155D.

*Reproductive organs.*—Androecium: Present on disc florets only. Anther color: 9A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct culivar of Chrysanthemum plant named 'Yokey West', as illustrated and described.

* * * * *

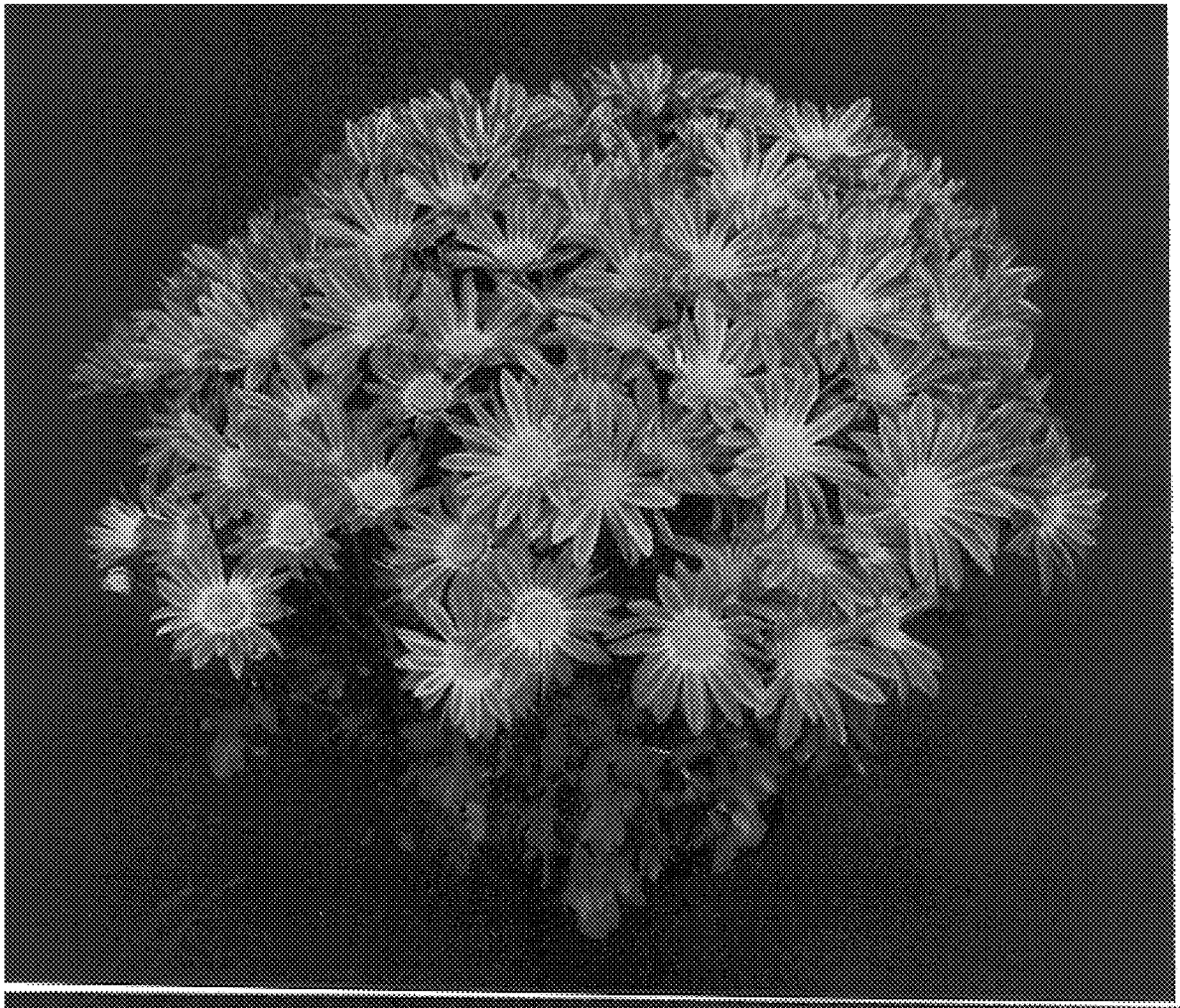
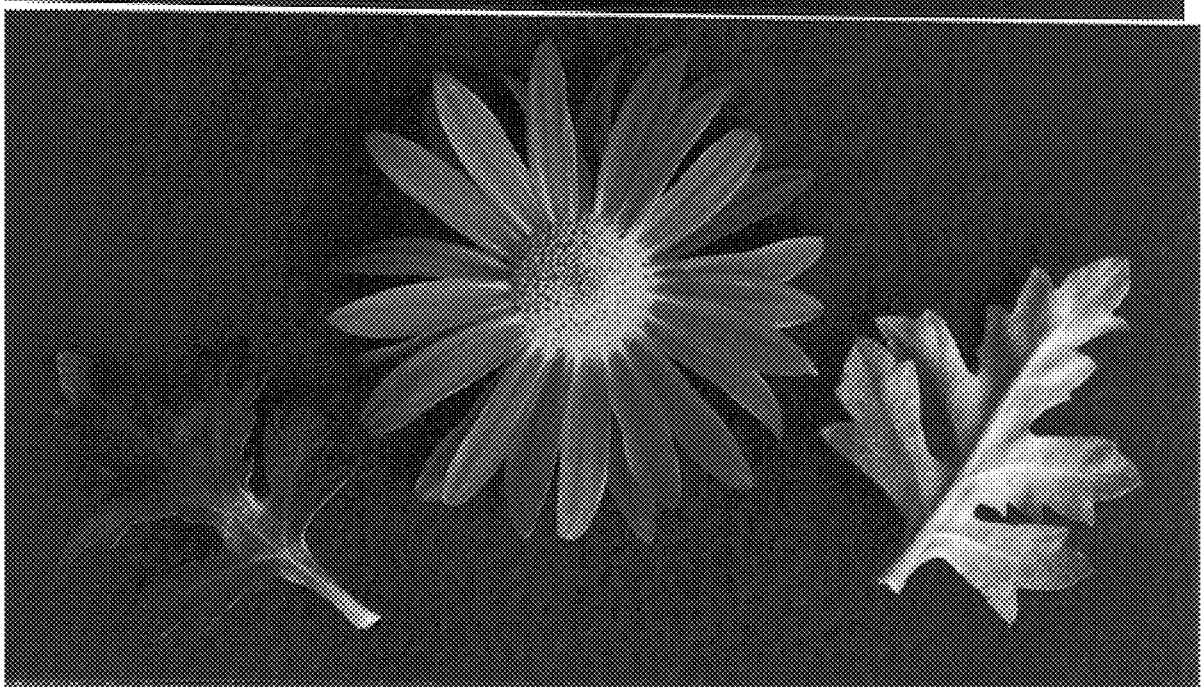

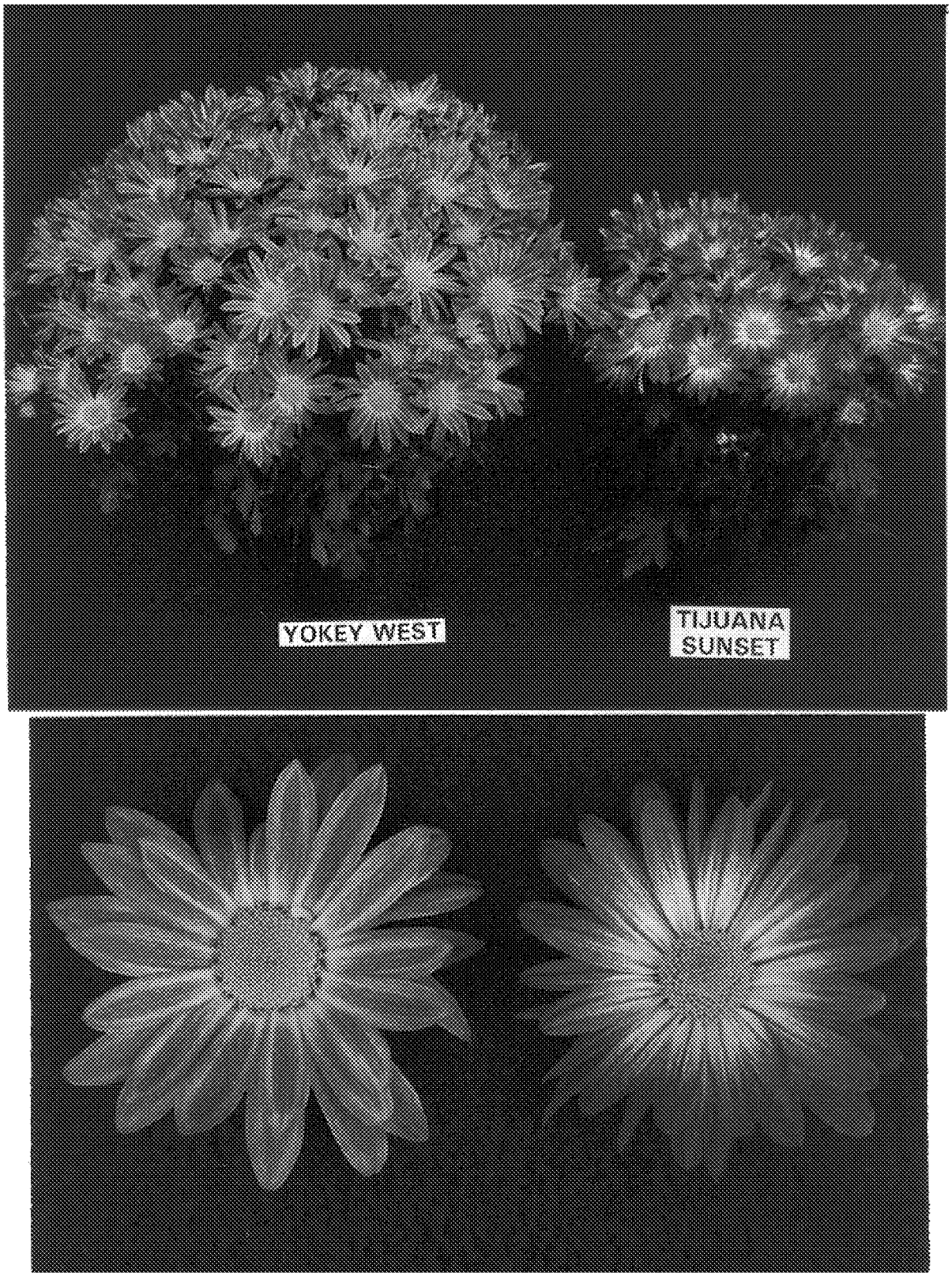
YOKEY WEST
TIJUANA
SUNSET